US011532386B2

(12) United States Patent
Petri et al.

(10) Patent No.: US 11,532,386 B2
(45) Date of Patent: Dec. 20, 2022

(54) GENERATING AND CUSTOMIZING SUMMARIZED NOTES

(71) Applicant: INTERNATIONAL BUSINESS MACHINES CORPORATION, Armonk, NY (US)

(72) Inventors: John E. Petri, St. Charles, MN (US); David R. Stanich, Rochester, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 352 days.

(21) Appl. No.: 16/359,826

(22) Filed: Mar. 20, 2019

(65) Prior Publication Data
US 2020/0303048 A1 Sep. 24, 2020

(51) Int. Cl.
| | | |
|---|---|---|
| *G16H 15/00* | (2018.01) | |
| *G06N 20/00* | (2019.01) | |
| *G06F 40/47* | (2020.01) | |
| *G06F 40/56* | (2020.01) | |
| *G06F 40/58* | (2020.01) | |
| *G06F 40/186* | (2020.01) | |
| *G06F 40/274* | (2020.01) | |

(52) U.S. Cl.
CPC ........... *G16H 15/00* (2018.01); *G06F 40/186* (2020.01); *G06F 40/274* (2020.01); *G06F 40/47* (2020.01); *G06F 40/56* (2020.01); *G06F 40/58* (2020.01); *G06N 20/00* (2019.01)

(58) Field of Classification Search
None
See application file for complete search history.

(56) References Cited

U.S. PATENT DOCUMENTS

| | | |
|---|---|---|
| 9,805,160 B2 | 10/2017 | Morris et al. |
| 2003/0105638 A1 | 6/2003 | Taira |
| 2014/0181128 A1* | 6/2014 | Riskin ................. G06F 16/3344 |
| | | 707/756 |
| 2016/0019299 A1* | 1/2016 | Boloor .................... G06F 16/36 |
| | | 705/3 |

(Continued)

FOREIGN PATENT DOCUMENTS

WO     WO-2014031541 A2 *   2/2014   ............. G06F 19/00

OTHER PUBLICATIONS

Devarakonda, M.V., et al., "Automated Problem List Generation and Physicians Perspective from a Pilot Study", International Journal of Medical Informatics, 105, [online], © 2017, [retrieved on Mar. 20, 2019], Retrieved from the Internet at <URL: https://www.sciencedirect.com/science/article/pii/S1386505617301648>, 9 pp.

(Continued)

*Primary Examiner* — Rachelle L Reichert
(74) *Attorney, Agent, or Firm* — Konrad Raynes Davda & Victor LLP; Janaki K. Davda

(57) ABSTRACT

Provided are techniques for generating and customizing summarized notes. A template is selected from a plurality of templates based on a context using a machine learning model. The template includes one or more translatable string resources with variables to represent key attributes extracted from historical notes. A summarized note is generated using values of the key attributes for the variables in the translatable string resources of the template.

18 Claims, 9 Drawing Sheets

(56) References Cited

U.S. PATENT DOCUMENTS

| | | | |
|---|---|---|---|
| 2016/0239608 A1 | 8/2016 | Cederstrom et al. | |
| 2017/0235888 A1 | 8/2017 | Rahman et al. | |
| 2017/0270250 A1 | 9/2017 | Dettman et al. | |
| 2017/0364640 A1* | 12/2017 | Badawi | G16H 10/60 |
| 2018/0157724 A1* | 6/2018 | Kinsely | G06F 16/254 |
| 2020/0176098 A1* | 6/2020 | Lucas | G16H 70/40 |
| 2021/0374812 A1* | 12/2021 | Hoang | G06N 20/00 |

OTHER PUBLICATIONS

Harris, M.D., "Building a Large-Scale Commercial NLG System for an EMR", [online], [Retrieved on Mar. 20, 2019], Retrieved from the Internet at <URL: http://www.aclweb.org/anthology/W08-1120>, 4 pp.

Health IT Outcomes, "Patient Logic Launches Next-Generation Physician Documentation System", [online], Apr. 24, 2013 [Retrieved on Mar. 20, 2019], Retrieved from the Internet at <URL: https://www.healthitoutcomes.com/doc/patient-logic-launches-generationphysician-documentation-system-0001>, 2 pp.

Mell, P., et al., "Effectively and Securely Using the Cloud Computing Paradigm", NIST, Information Technology Laboratory, Oct. 7, 2009, 80 pp.

Mell, P., et al., "The NIST Definition of Cloud Computing", NIST, Special Publication 800-145, Sep. 2011, 7 pp.

Meystre, S., et al., "Natural Language Processing to Extract Medical Problems from Electronic Clinical Documents: Performance Evaluation", Journal of Biomedical Informatics, vol. 39, Issue 6, Dec. 2006, 11 pp.

Nuance Communications, "Computer-Assisted Physician Documentation Powered by AI", [online], © 2019 Nuance Communications, Inc., [Retrieved on Mar. 20, 2019], Retrieved from the Internet at <URL: https://www.nuance.com/healthcare/clintegrity/documentationimprovement/computer-assisted-physician-documentation.html>, 6 pp.

Savova, G.K., et al., "Mayo Clinical Text Analysis and Knowledge Extraction System (cTAKES): Architecture, Component Evaluation and Applications", Journal of the American Medical Informatics Association, vol. 17, Issue 5, Sep. 2010, 7 pp.

\* cited by examiner

```
{
  "operator": "AND",
  "conditions": [
    {
      "attributeIdentifier": "Menopausal",
      "operator": "NE",
      "value": "NULL"
    },
    {
      "attributeIdentifier": "CancerStage",
      "operator": "NE",
      "value": "NULL"
    },
    {
      "attributeIdentifier": "CancerType",
      "operator": "NE",
      "value": "NULL"
    },
    {
      "attributeIdentifier": "$Inflammatory",
      "operator": "EQ",
      "value": "yes"
    },
    {
      "attributeIdentifier": "MCategory",
      "operator": "NE",
      "value": "M1"
    }
  ]
)
```

Input Data (Values for Key Attributes):

Menopausal=pre
CancerStage=II
CancerType=Breast
EstrogenReceptorStatus=positive
ProgesteroneReceptorStatus=negative
HER2Status=positive
PriorChemotherapyRegimen=RegimenA
TimeSinceChemotherapy=6

Summarized Note:

The patient is pre-menopausal with stage II breast cancer. Test results show ER+, PR-, HER2+. The patient has received RegimentA 6 months ago.

FIG. 5

GENERATING AND CUSTOMIZING SUMMARIZED NOTES

BACKGROUND

1. Field of the Invention

Embodiments of the invention relate to generating and customizing summarized notes. Certain embodiments of the invention relate to intelligent generation and customization of summarized notes from patient attributes and history.

2. Description of the Related Art

Some medical systems help physicians identify key information in a patient's medical record, surface relevant evidence, and explore treatment options. Some patient attributes may be extracted using Natural Language Processing (NLP).

However, often users enter attributes manually ("by hand") through a more traditional form-based User Interface (UI). Manual entry may be prevalent in many international hospitals that do not have standard electronic medical records.

Regardless of whether the information is processed by NLP or entered manually, the result is a set of structured data used to analyze a patient's case and suggest treatment options. While structured data makes it easier to provide treatment options, it may be time consuming for a care team to sort through the various categories of information when trying to understand or share a case.

SUMMARY

In accordance with embodiments, a computer-implemented method is provided for generating and customizing summarized notes. The computer-implemented method comprises operations. A template is selected from a plurality of templates based on a context using a machine learning model. The template includes one or more translatable string resources with variables to represent key attributes extracted from historical notes. A summarized note is generated using values of the key attributes for the variables in the translatable string resources of the template.

In accordance with other embodiments, a computer program product is provided for generating and customizing summarized notes. The computer program product comprises a computer readable storage medium having program code embodied therewith, the program code executable by at least one processor to perform operations. A template is selected from a plurality of templates based on a context using a machine learning model. The template includes one or more translatable string resources with variables to represent key attributes extracted from historical notes. A summarized note is generated using values of the key attributes for the variables in the translatable string resources of the template.

In accordance with yet other embodiments, a computer system is provided for generating and customizing summarized notes. The computer system comprises one or more processors, one or more computer-readable memories and one or more computer-readable, tangible storage devices; and program instructions, stored on at least one of the one or more computer-readable, tangible storage devices for execution by at least one of the one or more processors via at least one of the one or more memories, to perform operations. A template is selected from a plurality of templates based on a context using a machine learning model. The template includes one or more translatable string resources with variables to represent key attributes extracted from historical notes. A summarized note is generated using values of the key attributes for the variables in the translatable string resources of the template.

Thus, embodiments advantageously generate a summarized note that is based on a template so that the summarized note may be customized (e.g., for a physician, a patient or a care team).

In other embodiments, the historical notes are ingested, sentence composition information is extracted from the historical notes, distribution patterns of the key attributes in the historical notes are identified, and characteristics of the historical notes are identified. The translatable string resources represent the characteristics using the sentence composition information and the distribution patterns. This advantageously allows for the summarized note to include sentences that are customized based on the characteristics, the sentence composition information, and the distribution patterns.

In additional embodiments, the distribution patterns are identified using a distribution machine learning model. This advantageously allows for use of the distribution machine learning model.

In yet additional embodiments, the characteristics are identified using a characteristics machine learning model. This advantageously allows for use of the characteristics machine learning model.

In further embodiments, the one or more translatable string resources are generated using a string machine learning model. This advantageously allows for use of the string machine learning model.

In yet further embodiments, the one or more translatable string resources are selected for the template using rules. This advantageously allows for further customization of the summarized note by using rules, which may be modified, to select particular translatable string resources for the template.

In yet other embodiments, the translatable string resources in the template are translated from a first language to a second language; and the summarized note is generated in the second language. This advantageously allows for generating the summarized note in any language.

Moreover, in embodiments, a Software as a Service (SaaS) is configured to perform operations of the computer-implemented method. This advantageously allows for embodiments in a cloud computing environment.

BRIEF DESCRIPTION OF THE SEVERAL VIEWS OF THE DRAWINGS

Referring now to the drawings in which like reference numbers represent corresponding parts throughout:

FIG. 4 illustrates an example translatable string resource in accordance with certain embodiments.

FIG. 5 illustrates generation of a summarized note given input data in accordance with certain embodiments.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Figure 1:
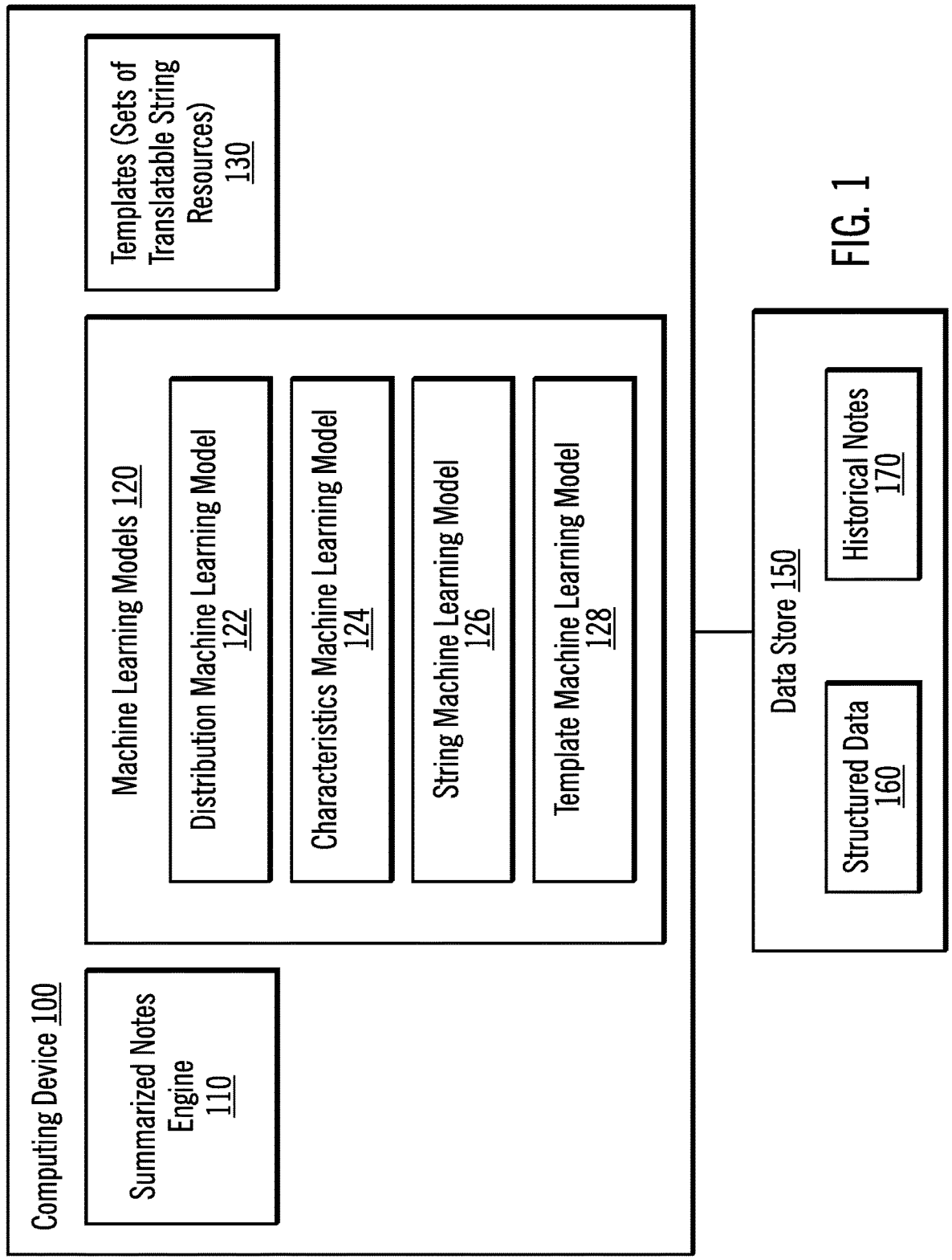
FIG. 1 illustrates, in a block diagram, a computing environment in accordance with certain embodiments.

FIG. 1 illustrates, in a block diagram, a computing environment in accordance with certain embodiments. A computing device 100 is coupled to a data store 150. The computing device 100 includes a summarized notes engine 110, machine learning models 120, and templates 130 that are used to create summarized notes. A template 130 may be described as a set of translatable string resources. A translatable string resource may be described as a sentence with variables for storing key attributes. In certain embodiments, there may be a template for a patient, a type of disease, a template for a type of a template for a doctor, a template for an institution, etc.

In certain embodiments, the machine learning models 120 include a distribution machine learning model 122, a characteristics machine learning model 124, a string machine learning model 126, and a template machine learning model 128.

The data store 150 includes structured data 160 and historical notes 170. In certain embodiments, the structured data includes key attributes extracted by the summarized notes engine 110 using natural language processing or received by the summarized notes engine 110 via a form-based User Interface (UI). The historical notes 170 may be unstructured data, which may be described as notes that are dictated or written by the doctor. For example, the historical notes 170 may include clinical notes created (e.g., written or dictated) by a doctor about one or more patients over a period of time. In certain embodiments, information extracted from the historical notes 170 is saved in a structured form.

The summarized notes engine 110 generates and customizes (using the templates 130) summarized notes. For example, the summarized notes engine 110 may generate patient summaries specifically tailored to the patients.

The summarized notes engine 110 dynamically generates and customizes summarized notes that are tailored for a physician, a patient or a care team. The summarized notes engine 110 takes into account characteristics, such as writing style, order of information, preferred length of the summarized note, and cultural differences.

In certain embodiments, the summarized notes engine 110 uses the template machine learning model 128 to select a template for generating the summarized notes for a given context. A context may include a patient, a doctor, an institution or a multi-disciplinary care team. The template machine learning model 128 is trained based on several prior summarized notes written in different contexts. When a similar context is subsequently encountered by the summarized notes engine 110, the summarized notes engine 110 employs the template machine learning model 128 to identify the template 130 that most closely matches the context. In this way, embodiments of the invention are not constrained by a static set of templates or rules. Thus, the template machine learning model 128 automates the use of templates.

Figure 2:
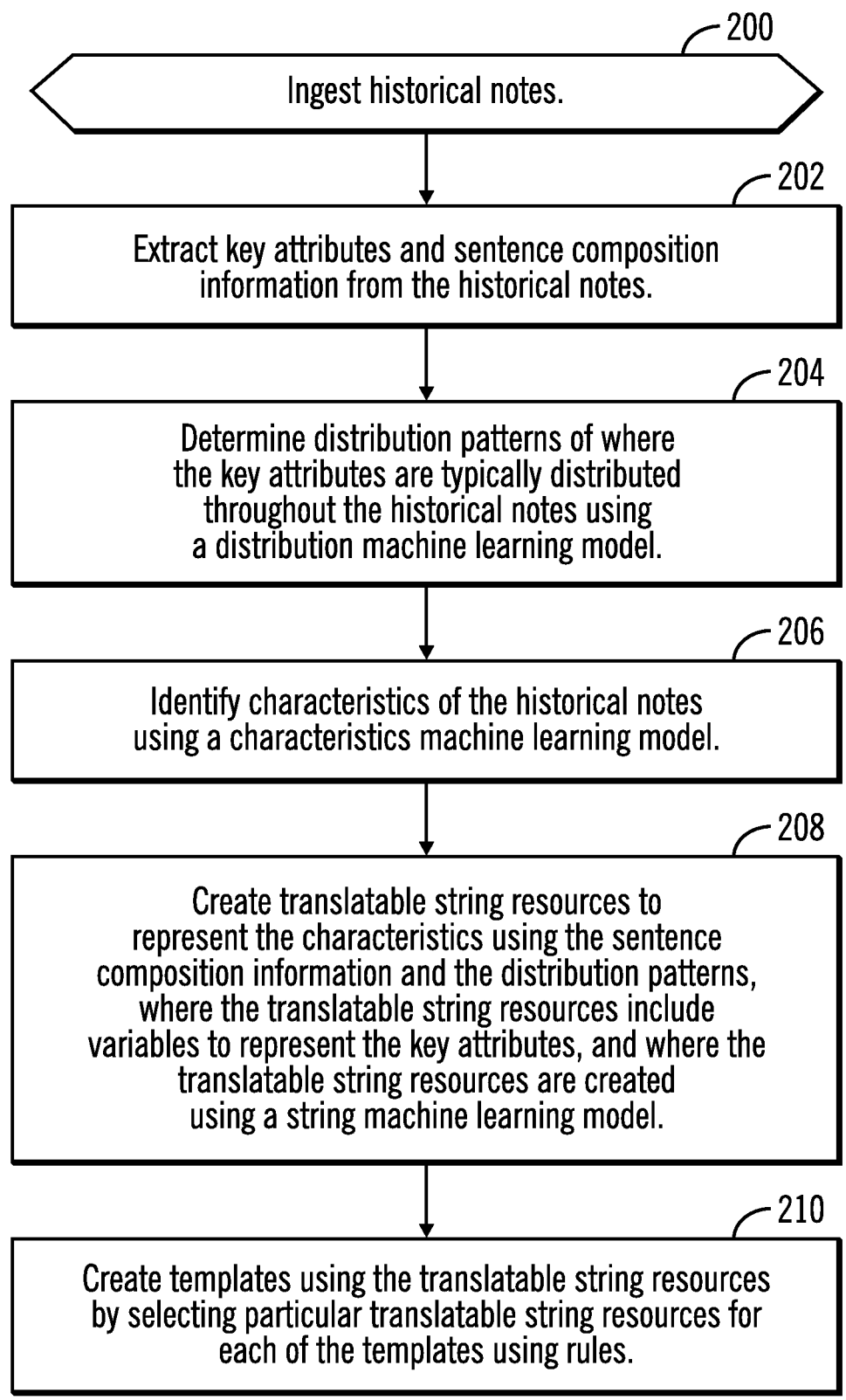
FIG. 2 illustrates, in a flowchart, operations for creating templates in accordance with certain embodiments.

FIG. 2 illustrates, in a flowchart, operations for creating templates in accordance with certain embodiments. Control begins at block 200 with the summarized notes engine 110 ingesting historical notes. In certain embodiments, the summarized notes engine 110 ingests historical notes from a particular physician or institution.

In block 202, the summarized notes engine 110 extracts key attributes and sentence composition information from the historical notes. In certain embodiments, the historical notes are run through natural language processing to extract the key attributes and the sentence composition information (e.g. a grammar parse tree). In certain embodiments, the key attributes may be described as ones that are frequently found. In other embodiments, the key attributes may be ones that are common across the historical notes. In yet other embodiments, the key attributes may be ones that are identified based on pre-defined rules, which may be modified. In block 204, the summarized notes engine 110 determines distribution patterns of where attributes are typically (commonly) distributed throughout the historical notes using the distribution machine learning model 122. In certain embodiments, the summarized notes engine 110 uses the distribution machine learning model 122 with supervised or unsupervised learning techniques to determine the most common distribution patterns of the key attributes throughout the historical notes. For example, unsupervised learning may be used to identify where the key attributes tend to be clustered throughout the historical notes.

In certain embodiments, the summarized notes engine 110 determines that the key attributes of a patient history, prior therapies, and status of tests (e.g., HER2 status) are commonly found in the first sentence or first paragraph of a historical note.

In block 206, the summarized notes engine 110 identifies characteristics of the historical notes using the characteristics machine learning model 124. In certain embodiments, characteristics, such as sentence style (e.g. concise data points versus more natural, complete sentences), length (e.g. 5 sentences versus 10 sentences), etc. are also learned from the historical notes. With embodiments, the summarized notes engine 110 uses the characteristics machine learning model 124 to learn the characteristics for different contexts. In block 208, the summarized notes engine 110 creates translatable string resources to represent the characteristics using the sentence composition information and the distribution patterns, where the translatable string resources include variables to represent the key attributes, and where the translatable string resources are created using a string machine learning model 126. In certain embodiments, the translatable string resources are complete sentences with substitution variables into which the key attributes may be inserted. There may be multiple types of translatable string resources (e.g., for different writing styles, different string types depending on plural words and/or other factors for proper translation into other languages, etc.).

In block 210, the summarized notes engine 110 creates templates using the translatable string resources by selecting particular translatable string resources for each of the templates using rules. The rules may be modified to customize selection of the templates. For example, one template may have one set of translatable string resources for a patient, while another template has a different set of translatable string resources for a doctor. In another example, a first template may be used to generated summarized notes for accountants (who are not allowed access to health care information or are allowed limited access to the health care information) in a company, while a second template may be used to generate summarized notes for human resources managers (who are allowed access to health care information). In yet another example, a first template may be used to generate summarized notes for posting on a social media site (e.g. for viewing by family and friends), and a second template may be used to generate summarized notes for providing to colleagues. In yet a further example, a first template may be used to generate summarized notes for a surgical oncologist (who may prefer to see particular attributes related to surgery displayed prominently), while a second template may be used to generate summarized notes for a general oncologist.

In certain embodiments, the summarized notes engine 110 automatically generates the summarized note after creating the templates. In certain embodiments, the summarized note may be described as having one or more sentences. In certain embodiments, the summarized note may be described to be in a normalized format.

Figure 3:
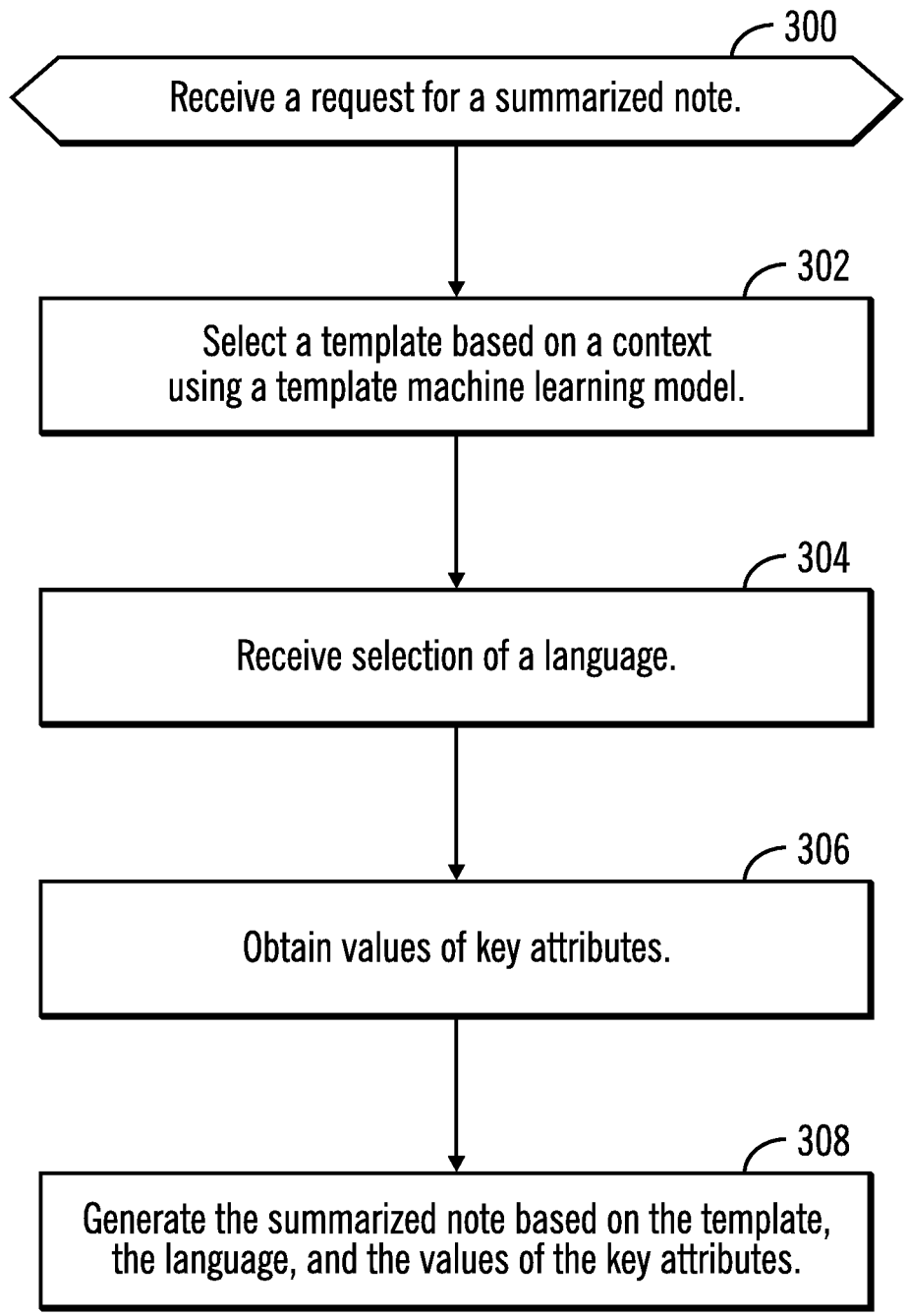
FIG. 3 illustrates, in a flowchart, operations for generating and customizing summarized notes in accordance with certain embodiments.

FIG. 3 illustrates, in a flowchart, operations for generating and customizing summarized notes in accordance with certain embodiments. Control begins at block 300 with the summarized notes engine 110 receiving a request for a summarized note. In block 302, the summarized notes engine 110 selects a template based on a context using the template machine learning model 128. That is, in certain embodiments, the template machine learning model 128, which has been trained on various contexts, is used to select the template 130 that most closely matches (i.e., best matches) the context. In certain additional embodiments, a user is provided the selected template and asked to either select that template or another template. In yet other embodiments, the user is allowed to modify the selected template. In certain embodiments, the summarized notes engine 110 determines the context. In other embodiments, the context is provided with the request for the summarized note.

In block 304, the summarized notes engine 110 receives selection of a language. In block 306, the summarized notes engine 110 obtains values (input data) of key attributes. In block 308, the summarized notes engine 110 generates the summarized note based on the template, the language, and the values of the key attributes.

In certain embodiments, the translatable string resources in the selected template are translated from an original (first) language to the selected (second) language, and the summarized note is generated in the selected language.

In certain embodiments, the summarized notes engine 110 uses the string machine learning model 126 to generate the translatable string resources. That is, in certain embodiments, the string machine learning model 126, which has been trained on various inputs, is used to select one or more translatable string resources for a template. In certain additional embodiments, a user is provided the selected one or more translatable string resources and asked to either select those one or more translatable string resources or one or more other translatable string resources. In yet other embodiments, the user is allowed to modify the selected one or more translatable string resources.

For example, based on inputs, the following translatable string resource may be generated, where {VALUE} represents a structured value that is to be replaced with the value of a key attribute.

The patient is a {PatientAge}-year-old {Menopausal} with stage {CancerStage} inflammatory {CancerType}.

In certain embodiments, the translatable string resource may be selected to be part of a template 130 for a patient note based on one or more rules.

FIG. 4 illustrates an example translatable string resource 400 in accordance with certain embodiments. The rule 400 identifies the key attributes whose values are to be added.

FIG. 5 illustrates generation of a summarized note given input data in accordance with certain embodiments. In FIG. 5, given the input data 500 providing values for the key attributes, the summarized notes engine 110 generates the summarized note 550 using the translatable string resource 400. In certain embodiments, the input data is structured data.

Figure 6:
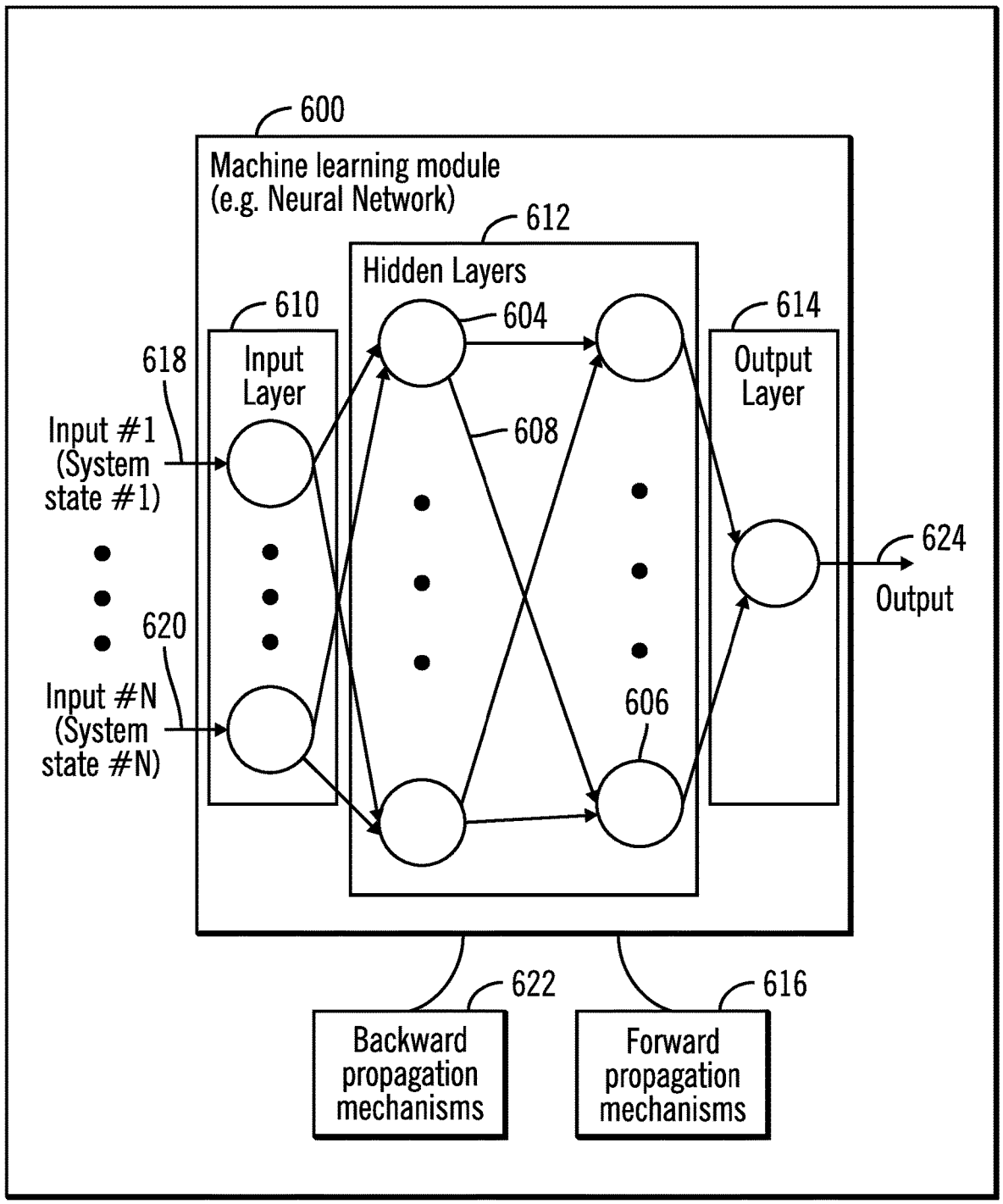
FIG. 6 illustrates, in a block diagram, details of a machine learning model in accordance with certain embodiments.

FIG. 6 illustrates, in a block diagram, details of a machine learning model 600 in accordance with certain embodiments. Each of the machine learning models 120 may take the form of machine learning model 600. The machine learning model 600 may comprise a neural network with a collection of nodes with links connecting them, where the links are referred to as connections. For example, FIG. 6 shows a node 604 connected by a connection 608 to the node 606. The collection of nodes may be organized into three main parts: an input layer 610, one or more hidden layers 612, and an output layer 614.

The connection between one node and another is represented by a number called a weight, where the weight may be either positive (if one node excites another) or negative (if one node suppresses or inhibits another). Training the machine learning model 600 entails calibrating the weights in the machine learning model 600 via mechanisms referred to as forward propagation 616 and backward propagation 622. Bias nodes that are not connected to any previous layer may also be maintained in the machine learning model 600. A bias may be described as an extra input of 1 with a weight attached to it for a node.

In forward propagation 616, a set of weights are applied to the input data 618 . . . 620 to calculate the output 624. For the first forward propagation, the set of weights may be selected randomly or set by, for example, a system administrator.

In backward propagation 622 a measurement is made for a margin of error of the output 624, and the weights are adjusted to decrease the error. Backward propagation 622 compares the output that the machine learning model 600 produces with the output that the machine learning model 600 was meant to produce, and uses the difference between them to modify the weights of the connections between the nodes of the machine learning model 600, starting from the output layer 614 through the hidden layers 612 to the input layer 610, i.e., going backward in the machine learning model 600. In time, backward propagation 622 causes the machine learning model 600 to learn, reducing the difference between actual and intended output to the point where the two come very close or coincide. Thus, the machine learning model 600 is configured to repeat both forward and backward propagation until the weights of the machine learning model 600 are calibrated to accurately predict an output.

As an example, a distribution machine learning model 122 taking the form of the machine learning model 600 receives inputs of historical notes and key attributes and outputs distribution patterns of where the key attributes are typically distributed throughout the historical notes.

As another example, a characteristics machine learning model 124 taking the form of machine learning model 600 receives as input historical notes and contexts and outputs characteristics for the contexts. Thus, the characteristics machine learning model 124 is used to learn the characteristics for different contexts.

As a further example, a string machine learning model 126 taking the form of machine learning model 600 receives inputs of characteristics, sentence composition information, distribution patterns, and variables to represent key attributes, and outputs translatable string resources. Thus, characteristics, sentence composition information, distribution patterns, and variables to represent key attributes may be incorporated into translatable string resources via the string machine learning model 126.

As yet another example, a template machine learning model 128 taking the form of machine learning model 600 receives an input of a context and outputs a template to use for the context.

Physicians may prefer and may be more efficient at consuming information through a summarized note. Different physicians or institutions have their own writing styles and ways of organizing information which they prefer to use in notes. Also, when one physician refers a patient to receiving physician, who prefers a different way of viewing the information, that receiving physician may create a new note.

The amount of information available to inform care decisions is growing exponentially. Yet the time needed to consume this information (e.g., locating insights specific to each patient's unique needs to potentially improve treatment outcomes) may be limited.

Thus, the summarized notes engine 110 generates and customizes summarized notes that may be shared by physicians and teams.

In certain embodiments, a plurality of historical notes ("clinical note summaries") are ingested using Natural Language Processing (NLP) on the historical notes to extract key patient attributes and sentence composition information. A most common distribution of the key patient attributes throughout the historical notes is determined. Based on the most common distribution of the key patient attributes, a set of translatable string resources are created with variables for storing the key patient attributes. Summarized notes are generated using the set of translatable string resources and values of the key patient attributes.

Figure 7:
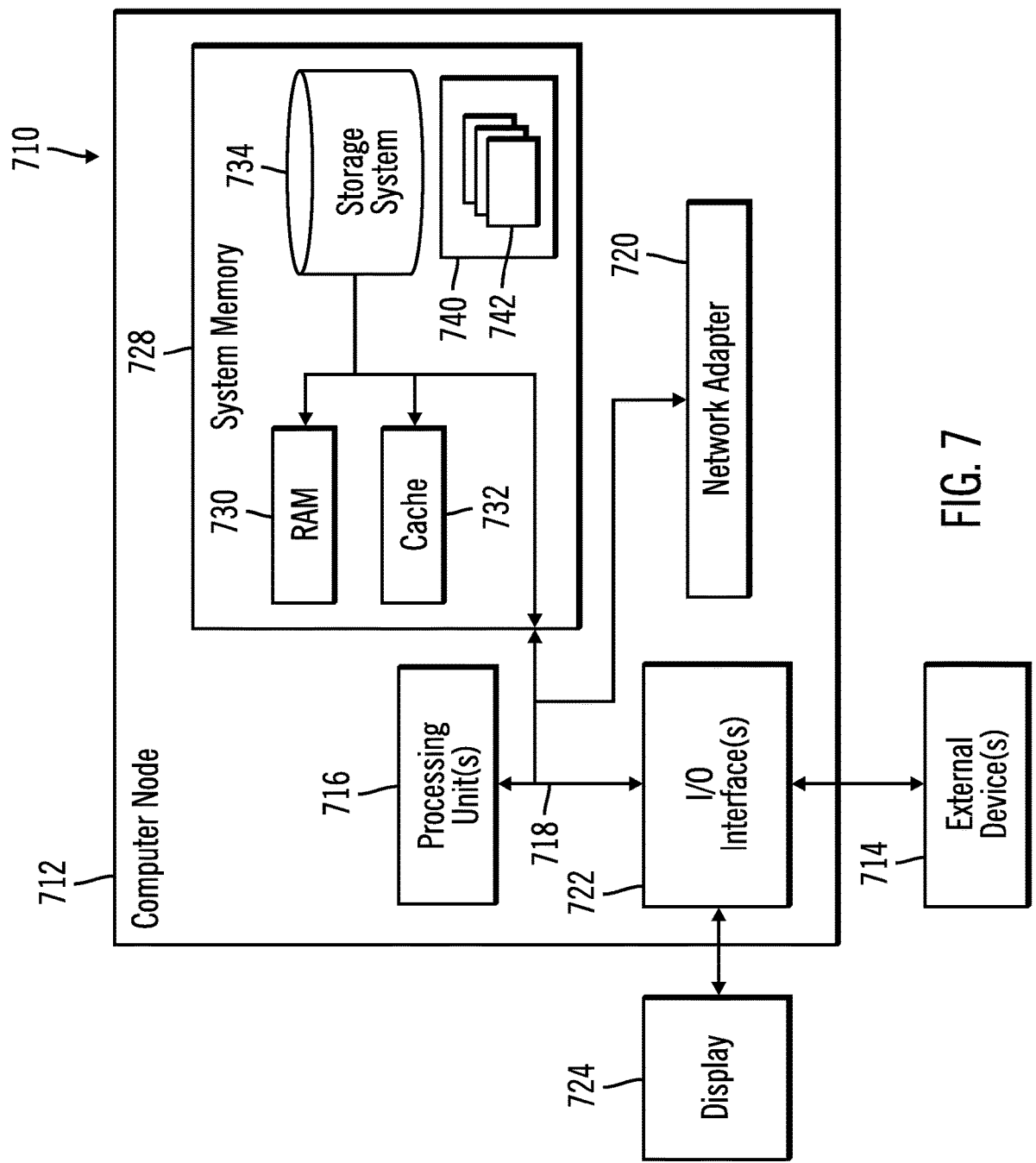
FIG. 7 illustrates a computing node in accordance with certain embodiments.

FIG. 7 illustrates a computing environment 710 in accordance with certain embodiments. In certain embodiments, the computing environment is a cloud computing environment. Referring to FIG. 7, computer node 712 is only one example of a suitable computing node and is not intended to suggest any limitation as to the scope of use or functionality of embodiments of the invention described herein. Regardless, computer node 712 is capable of being implemented and/or performing any of the functionality set forth hereinabove.

The computer node 712 may be a computer system, which is operational with numerous other general purpose or special purpose computing system environments or configurations. Examples of well-known computing systems, environments, and/or configurations that may be suitable for use with computer node 712 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer node 712 may be described in the general context of computer system executable instructions, such as program modules, being executed by a computer system. Generally, program modules may include routines, programs, objects, components, logic, data structures, and so on that perform particular tasks or implement particular abstract data types. Computer node 712 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer node 712 is shown in the form of a general-purpose computing device. The components of computer node 712 may include, but are not limited to, one or more processors or processing units 716, a system memory 728, and a bus 718 that couples various system components including system memory 728 to one or more processors or processing units 716.

Bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer node 712 typically includes a variety of computer system readable media. Such media may be any available media that is accessible by computer node 712, and it includes both volatile and non-volatile media, removable and non-removable media.

System memory 728 can include computer system readable media in the form of volatile memory, such as random access memory (RAM) 730 and/or cache memory 732. Computer node 712 may further include other removable/non-removable, volatile/non-volatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 718 by one or more data media interfaces. As will be further depicted and described below, system memory 728 may include at least one program product having a set (e.g., at least one) of program modules that are configured to carry out the functions of embodiments of the invention.

Program/utility 740, having a set (at least one) of program modules 742, may be stored in system memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer node 712 may also communicate with one or more external devices 714 such as a keyboard, a pointing device, a display 724, etc.; one or more devices that enable a user to interact with computer node 712; and/or any devices (e.g., network card, modem, etc.) that enable computer node 712 to communicate with one or more other computing devices. Such communication can occur via Input/Output (I/O) interfaces 722. Still yet, computer node 712 can communicate with one or more networks such as a local area network (LAN), a general wide area network (WAN), and/or a public network (e.g., the Internet) via network adapter 720. As depicted, network adapter 720 communicates with the other components of computer node 712 via bus 718. It should be understood that although not shown, other hardware and/or software components could be used in conjunction with computer node 712. Examples, include, but are not limited to: microcode, device drivers, redundant processing units, external disk drive arrays, RAID systems, tape drives, and data archival storage systems, etc.

In certain embodiments, the computing device 100 has the architecture of computer node 1012. In certain embodiments, the computing device 100 is part of a cloud infrastructure. In certain alternative embodiments, the computing device 100 is not part of a cloud infrastructure.

Cloud Embodiments

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
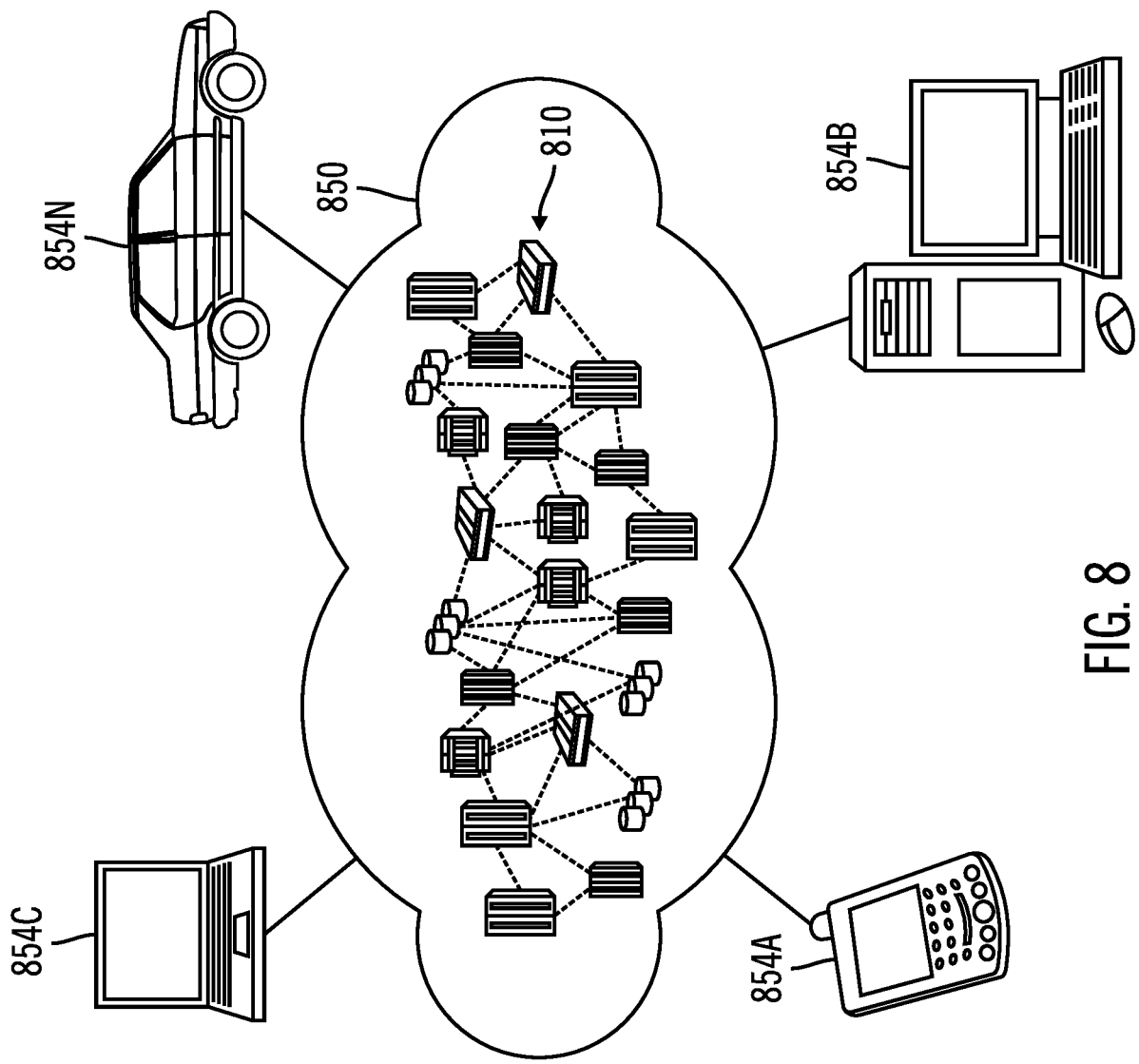
FIG. 8 illustrates a cloud computing environment in accordance with certain embodiments.

Referring now to FIG. 8, illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Nodes 810 may communicate with one another. They may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
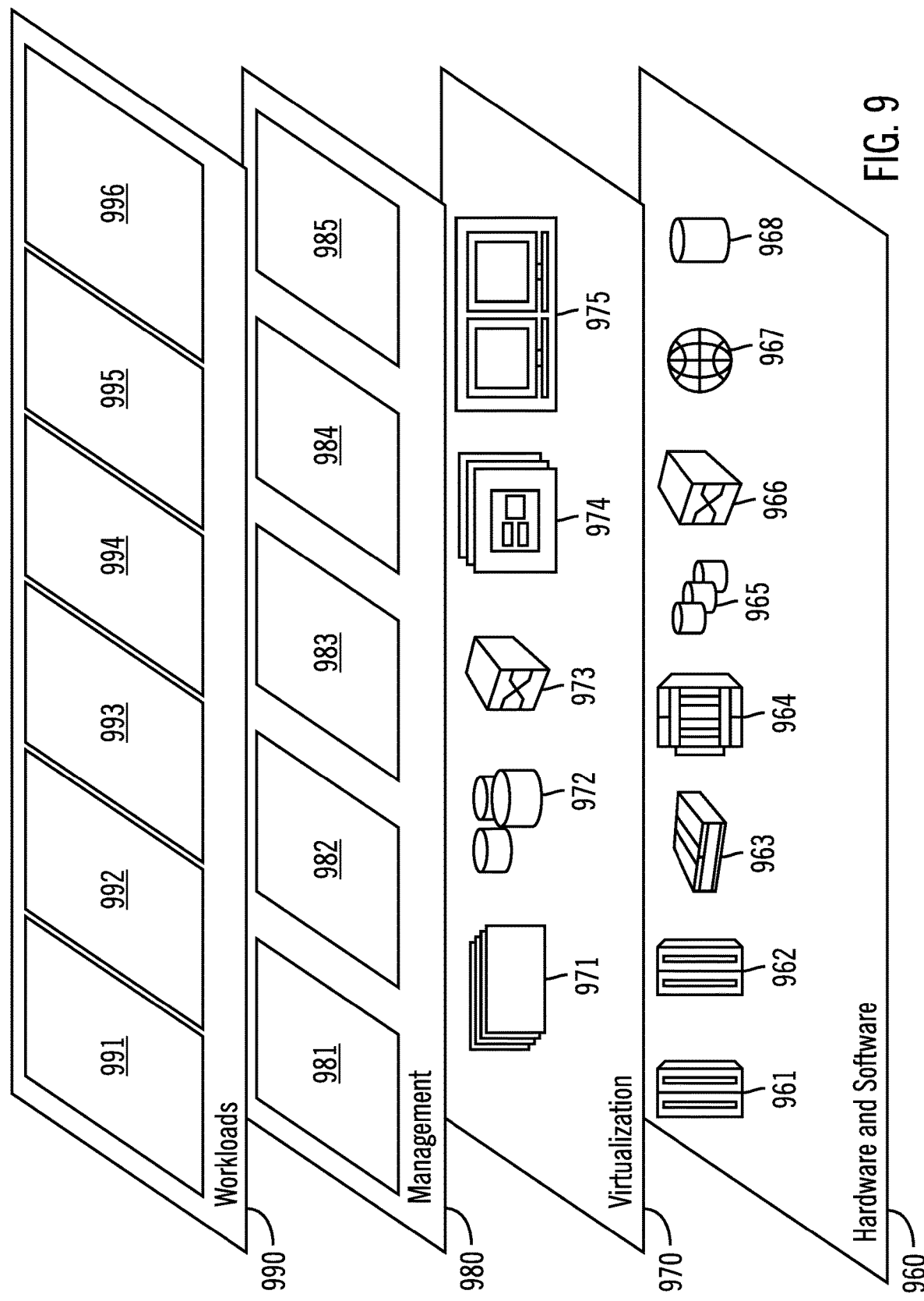
FIG. 9 illustrates abstraction model layers in accordance with certain embodiments.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 includes hardware and software components. Examples of hardware components include: mainframes 961; RISC (Reduced Instruction Set Computer) architecture based servers 962; servers 963; blade servers 964; storage devices 965; and networks and networking components 966. In some embodiments, software components include network application server software 967 and database software 968.

Virtualization layer 970 provides an abstraction layer from which the following examples of virtual entities may be provided: virtual servers 971; virtual storage 972; virtual networks 973, including virtual private networks; virtual applications and operating systems 974; and virtual clients 975.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Examples of workloads and functions which may be provided from this layer include: mapping and navigation 991; software development and lifecycle management 992; virtual classroom education delivery 993; data analytics processing 994; transaction processing 995; and generation and customization of summarized notes 996

Thus, in certain embodiments, software or a program, implementing generating and customizing summarized notes in accordance with embodiments described herein, is provided as a service in a cloud environment.

Additional Embodiment Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The foregoing description provides examples of embodiments of the invention, and variations and substitutions may be made in other embodiments.

What is claimed is:

1. A computer-implemented method, comprising operations for:
   using a distribution machine learning model to output distribution patterns, wherein the distribution machine learning model receives inputs of historical notes and attributes, and wherein the distribution patterns indicate where the attributes are distributed throughout the historical notes;
   using a characteristics machine learning model to output characteristics, wherein the characteristics machine learning model receives as input the historical notes and contexts, and wherein the characteristics are for the contexts;
   using a string machine learning model to generate translatable string resources, wherein the string machine learning model receives inputs of sentence composition information, the distribution patterns output from the distribution machine learning model, the characteristics output from the characteristics machine learning model, and variables to represent attributes, and outputs the translatable string resources with the variables to represent the attributes, wherein each translatable string resource of the translatable string resources comprises a sentence with one or more of the variables;
   creating a plurality of templates using the translatable string resources output by the string machine learning model by selecting a different set of the translatable string resources for each of the templates;
   using a template machine learning model to output a first template from the plurality of templates, wherein the template machine learning model receives as input a first context of the contexts;
   generating a first summarized note using values of the attributes for the variables in the translatable string resources of the first template;
   using the template machine learning model to output a second template from the plurality of templates, wherein the template machine learning model receives as input a second context of the contexts; and
   generating a second summarized note using values of the attributes for the variables in the translatable string resources of the second template.

2. The computer-implemented method of claim 1, further comprising:
   ingesting historical notes;
   extracting the sentence composition information from the historical notes;
   identifying the distribution patterns of the attributes in the historical notes; and
   identifying the characteristics of the historical notes, wherein the translatable string resources represent the characteristics using the sentence composition information and the distribution patterns.

3. The computer-implemented method of claim 1, wherein the translatable string resources are selected for a template of the plurality of templates using rules.

4. The computer-implemented method of claim 1, further comprising:
   translating the translatable string resources in a template of the plurality of templates from a first language to a second language; and
   generating a new summarized note in the second language.

5. The computer-implemented method of claim 1, wherein a Software as a Service (SaaS) is configured to perform the operations of the computer-implemented method.

6. The computer-implemented method of claim 1, wherein the distribution machine learning model, the characteristics machine learning model, the string machine learning model, and the template machine learning model each comprise a neural network.

7. A computer program product, the computer program product comprising a computer readable storage medium having program code embodied therewith, the program code executable by at least one processor to perform operations comprising:
  using a distribution machine learning model to output distribution patterns, wherein the distribution machine learning model receives inputs of historical notes and attributes, and wherein the distribution patterns indicate where the attributes are distributed throughout the historical notes;
  using a characteristics machine learning model to output characteristics, wherein the characteristics machine learning model receives as input the historical notes and contexts, and wherein the characteristics are for the contexts;
  using a string machine learning model to generate translatable string resources, wherein the string machine learning model receives inputs of sentence composition information, the distribution patterns output from the distribution machine learning model, the characteristics output from the characteristics machine learning model, and variables to represent attributes, and outputs the translatable string resources with the variables to represent the attributes, wherein each translatable string resource of the translatable string resources comprises a sentence with one or more of the variables;
  creating a plurality of templates using the translatable string resources output by the string machine learning model by selecting a different set of the translatable string resources for each of the templates;
  using a template machine learning model to output a first template from the plurality of templates, wherein the template machine learning model receives as input a first context of the contexts;
  generating a first summarized note using values of the attributes for the variables in the translatable string resources of the first template;
  using the template machine learning model to output a second template from the plurality of templates, wherein the template machine learning model receives as input a second context of the contexts; and
  generating a second summarized note using values of the attributes for the variables in the translatable string resources of the second template.

8. The computer program product of claim 7, wherein the program code is executable by the at least one processor to perform further operations comprising:
  ingesting historical notes;
  extracting the sentence composition information from the historical notes;
  identifying the distribution patterns of the attributes in the historical notes; and
  identifying the characteristics of the historical notes, wherein the translatable string resources represent the characteristics using the sentence composition information and the distribution patterns.

9. The computer program product of claim 7, wherein the translatable string resources are selected for a template of the plurality of templates using rules.

10. The computer program product of claim 7, wherein the program code is executable by the at least one processor to perform further operations comprising:
  translating the translatable string resources in a template of the plurality of templates from a first language to a second language; and
  generating a new summarized note in the second language.

11. The computer program product of claim 7, wherein a Software as a Service (SaaS) is configured to perform the operations of the computer program product.

12. The computer program product of claim 7, wherein the distribution machine learning model, the characteristics machine learning model, the string machine learning model, and the template machine learning model each comprise a neural network.

13. A computer system, comprising:
  one or more processors, one or more computer-readable memories and one or more computer-readable, tangible storage devices; and
  program instructions, stored on at least one of the one or more computer-readable, tangible storage devices for execution by at least one of the one or more processors via at least one of the one or more computer-readable memories, to perform operations comprising:
  using a distribution machine learning model to output distribution patterns, wherein the distribution machine learning model receives inputs of historical notes and attributes, and wherein the distribution patterns indicate where the attributes are distributed throughout the historical notes;
  using a characteristics machine learning model to output characteristics, wherein the characteristics machine learning model receives as input the historical notes and contexts, and wherein the characteristics are for the contexts;
  using a string machine learning model to generate translatable string resources, wherein the string machine learning model receives inputs of sentence composition information, the distribution patterns output from the distribution machine learning model, the characteristics output from the characteristics machine learning model, and variables to represent attributes, and outputs the translatable string resources with the variables to represent the attributes, wherein each translatable string resource of the translatable string resources comprises a sentence with one or more of the variables;
  creating a plurality of templates using the translatable string resources output by the string machine learning model by selecting a different set of the translatable string resources for each of the templates;
  using a template machine learning model to output a first template from the plurality of templates, wherein the template machine learning model receives as input a first context of the contexts;
  generating a first summarized note using values of the attributes for the variables in the translatable string resources of the first template;
  using the template machine learning model to output a second template from the plurality of templates, wherein the template machine learning model receives as input a second context of the contexts; and generating a second summarized note using values of the attributes for the variables in the translatable string resources of the second template.

14. The computer system of claim 13, wherein the operations further comprise:
ingesting historical notes;
extracting the sentence composition information from the historical notes;
identifying the distribution patterns of the attributes in the historical notes; and
identifying the characteristics of the historical notes, wherein the translatable string resources represent the characteristics using the sentence composition information and the distribution patterns.

15. The computer system of claim 13, wherein the operations further comprise:
translating the translatable string resources in a template of the plurality of templates from a first language to a second language; and
generating a new summarized note in the second language.

16. The computer system of claim 13, wherein a Software as a Service (SaaS) is configured to perform the operations of the computer system.

17. The computer system of claim 13, wherein the distribution machine learning model, the characteristics machine learning model, the string machine learning model, and the template machine learning model each comprise a neural network.

18. The computer system of claim 13, wherein the translatable string resources are selected for a template of the plurality of templates using rules.

* * * * *